US008309605B2

(12) United States Patent
Chang et al.

(10) Patent No.: US 8,309,605 B2
(45) Date of Patent: *Nov. 13, 2012

(54) ENHANCED BIMATOPROST OPHTHALMIC SOLUTION

(75) Inventors: Chin-Ming Chang, Tustin, CA (US); James N. Chang, Newport Beach, CA (US); Rhett M. Schiffman, Laguna Beach, CA (US); R. Scott Jordan, Trabuco Canyon, CA (US); Joan-En Chang-Lin, Tustin, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/965,514

(22) Filed: Dec. 10, 2010

(65) Prior Publication Data

US 2011/0124737 A1    May 26, 2011

Related U.S. Application Data

(63) Continuation of application No. 11/083,261, filed on Mar. 16, 2005, now Pat. No. 7,851,504.

(51) Int. Cl.
*A61K 31/19*     (2006.01)
*A61K 31/215*    (2006.01)

(52) U.S. Cl. ...................... 514/530; 514/573

(58) Field of Classification Search ............ 514/530, 514/573
See application file for complete search history.

(56) References Cited

U.S. PATENT DOCUMENTS

| | | |
|---|---|---|
| 4,055,602 A | 10/1977 | Nelson |
| 4,100,192 A | 7/1978 | Morozowich |
| 4,122,282 A | 10/1978 | Nelson |
| 4,123,441 A | 10/1978 | Johnson |
| 4,128,577 A | 12/1978 | Nelson |
| RE29,926 E | 3/1979 | Nelson |
| 4,171,331 A | 10/1979 | Biddlecom |
| 4,183,870 A | 1/1980 | Caton |
| 4,303,796 A | 12/1981 | Nelson |
| 4,382,953 A | 5/1983 | Ishii |
| 4,543,353 A | 9/1985 | Faustini |
| 4,599,353 A | 7/1986 | Bito |
| 4,812,457 A | 3/1989 | Narumiya |
| 4,994,274 A | 2/1991 | Chan |
| 5,034,413 A | 7/1991 | Chan |
| 5,281,591 A | 1/1994 | Burke |
| 5,352,708 A | 10/1994 | Woodward et al. |
| 5,474,979 A | 12/1995 | Ding |
| 5,510,383 A | 4/1996 | Bishop |
| 5,545,665 A | 8/1996 | Burk |
| 5,587,391 A | 12/1996 | Burk |
| 5,607,978 A | 3/1997 | Woodward |
| 5,688,819 A | 11/1997 | Woodward |
| 6,403,649 B1 | 6/2002 | Woodward |
| 6,596,765 B2 | 7/2003 | Ueno |
| 6,646,001 B2 | 11/2003 | Hellberg |
| 6,743,439 B1 | 6/2004 | Castillo |
| 6,933,289 B2 | 8/2005 | Lyons |
| 8,017,655 B2 | 9/2011 | Woodward |
| 2002/0103255 A1 | 8/2002 | Hellberg |
| 2004/0029771 A1 | 2/2004 | Rigdon |
| 2004/0115234 A1 | 6/2004 | Gewirtz |
| 2005/0004074 A1 | 1/2005 | Lyons |
| 2005/0276867 A1 | 12/2005 | Lyons |

FOREIGN PATENT DOCUMENTS

| | | |
|---|---|---|
| CA | 2144967 | 3/1994 |
| CA | 2498233 | 3/2004 |
| DE | 2 721 534 | 12/1977 |
| EP | 0 093 380 | 11/1983 |
| EP | 0 102 230 | 3/1984 |
| EP | 0098141 | 11/1984 |
| EP | 0 253 094 | 1/1988 |
| EP | 0 453 127 | 10/1991 |
| EP | 0 364 417 | 4/2004 |
| FR | 2239458 | 2/1975 |
| FR | 2 312 240 | 12/1976 |
| FR | 2 386 523 | 11/1978 |
| FR | 2 402 644 | 4/1979 |
| JP | S49-069636 | 7/1974 |
| JP | S62-215537 | 9/1987 |
| LU | 68 940 | 12/1973 |
| WO | WO90/02553 | 3/1990 |
| WO | WO 92-08465 | 5/1992 |
| WO | WO 94-006433 | 3/1994 |
| WO | WO 02-07731 | 1/2002 |
| WO | WO 2004-013119 | 2/2004 |

OTHER PUBLICATIONS

Higaki, Kazutaka; et al.: Estimation and Enhancement of In Vitro Corneal Transport of S-1033, a Novel Antiglaucoma Medication, International Journal of Pharmaceutics 132, 165-173 (1996).
Kaur, Indu Pal: et al. : Penetration Enhancer and Ocular Bioadhesives : Two New Avenues for Ophthalmic Drug Delivery. Drug Development and Industrial Pharmacy, 28 (4), 353-369 (2002).
Lumigan ®, 6 Pages, Jul. 2003.
Lumigan ® 0,1 mg/ml, 3 pages, Jan. 2010.
Xalatan ® Eye Drops, 3 pages, Retrieval Date : Oct. 2, 2010, http://home.intekom.com/pharm/pharmaca/xalatan.html.
Burstein, Neal; Preservative Alteration of Corneal Permeability in Humans and Rabbits, Investigative Ophthalmology & Visual Science, vol. 25, No. 12, Dec. 1984, pp. 1453-1457.
Curri, Joanne (Hi-Tech Pharmacal Co., Inc., Amityville, NY). Paragraph IV Letter to: Allergan, Inc. (Irvine, CA). 12 pages, Dec. 23, 2011.
Keller, N.; et al.: Increased Corneal Permeability Induced by the Dual Effects of Transient Tear Film Acidification and Exposure to Benzalkonium Chloride, Exp. Eye Res., vol. 30, 1980, pp. 203-210.
Lumigan® Label, Jul. 2003.

(Continued)

*Primary Examiner* — Zohreh Fay
(74) *Attorney, Agent, or Firm* — John E. Wurst; Doina G. Ene; Allergan, Inc.

(57) ABSTRACT

A composition comprising from 0.005% to 0.02% bimatoprost by weight and from 100 ppm to 250 ppm benzalkonium chloride, wherein said composition is an aqueous liquid which is formulated for ophthalmic administration is disclosed herein.

A method which is useful in treating glaucoma or ocular hypertension related thereto is also disclosed herein.

21 Claims, 2 Drawing Sheets

OTHER PUBLICATIONS

Bito, Laszlo et al., The Ocular Pharmacokinetics of Eicosanoids and Their Derivatives. 1. Comparison of Ocular Eicosanoid Penetration and Distribution Following the Topical Application of $PGF_{2\alpha}$, $PGF_{2\alpha}$-1-methyl Ester, and $PGF_{2\alpha}$-1-Isopropyl Ester, Exp. Eye Res., vol. 44, pp. 217-226 (1987).

Noecker, Robert et al., "Corneal and Conjunctival Changes Caused by Commonly Used Glaucoma Medications", Cornea, vol. 23, No. 5, pp. 490-496 (Jul. 2004).

Pfeiffer, N. et al., "New Development in Glaucoma Drug Therapy", Ophthalmology, vol. 89, pp. W1-W13 (1992).

Schumer, Robert et al., "Medical Treatment of Glaucoma", Ophthalmology, vol. 2, pp. 140-150 (1991).

Woodford, Roger et al., "Penetration Enhancers and the Percutaneous Absorption of Drugs : An Update", J. Toxicology-Cut. & Ocular Toxicology, vol. 5(3), pp. 167-177 (1986).

Burstein, Neal L. et al., "Electrophysiologic and Morphologic Effects of Ophthalmic Preparations on Rabbit Cornea Epithelium," Invest. Ophthalmol. Visual Sci., vol. 16, No. 10, 899-911, Oct. 1977.

Camber, Ola et al., "Influence of Some Preservatives on the Corneal Permeability of Pilocarpine and Dexamethasone, in Vitro", International Journal of Pharmaceutics, vol. 39, pp. 229-234 (1987).

Eisenberg. Dan et al., "Bimatoprost and Travoprost: A Review of Recent Studies of Two New Glaucoma Drugs", Survey of Ophthalmology, vol. 47, sup. 1, SI05-S115, Aug. 2002.

Green, Keith et al.. "Prednisolone Phosphate Penetration Into and Through the Cornea," Investigative Ophthalmology, vol. 13, No. 4, 316-319, Apr. 1974.

Lumigan® monograph in the 57th PDR (2003).

Mealy, N.E. et al., "Ophthalmic Drugs," Drugs of the Future, 27(5), 509-523, 2002.

Medical Review, Application No. 21-275, Center for Drug Evaluation and Research, 2001.

Pfister, Roswell R. et al., "The Effects of Ophthalmic Drugs, Vehicles, and Preservatives on Corneal Epithelium: a Scanning Electron Microscope Study," Effects of Ophthalmic Drugs, vol. 15, No. 4, 246-259, Apr. 1976.

Remington, The Science and Practice of Pharmacy, 20th ed. at 831 (2000).

Remington, The Science and Practice of Pharmacy, 21st ed. at 864 (2005).

Stewart, William et al., "Corneal Punctate Staining with Latanoprost, Bimatoprost, and Travoprost in Healthy Subjects", J. Glaucoma, vol. 12, No. 6.475'479, Dec. 2003.

Xalatan ® monograph in the 59th PDR (2005).

Arndt, H.C. et al., "The Synthesis and Biological Activity of Prostaglandins Analogs Containing Spirocyclic Rings," Prostaglandins, vol. 13, No. 5, Stoneham, MA, pp. 837-843 (May 1977).

Bito, LZ, Prostaglandins and Related Compounds as Potential Ocular Therapeutic Agents, Biological Protection with Prostaglandins, CRC Press Inc., pp. 231-252 (1985).

Bito, LZ, "Prostaglandins, Old Concepts and New Perspectives," Arch Oph., vol. 105, pp. 1036-1039 (Aug. 1987).

Brown, Michael, "Control of Contamination in Ophthalmic Solutions," 60 Proc. R. Soc. Med. 354 (1967).

Burstein, Neal, "Preservative Cytotoxic Threshold for Benzalkonium Chloride and Chlorhexidine Digluconate in Cat and Rabbit Corneas," 19(3) Invest. Opthal. & Visual Sci. 308 (1980).

Camras, Carl et al., "Reduction of Intraocular Pressure by Prostaglandins Applied Topically to the Eyes of Conscious Rabbits," 16 Invest. Ophthal. Visual Sci. 1125 (1977).

Camras, C.B. et al., "Reduction of Intraocular Pressure in Normal and Glaucomatous Primate (Aotus trivirgatus) Eyes by Topically Applied Prostaglandin F2α," 1 Current Eye Research 205-09, vol. 1, No. 4 (1981).

Center for Drug Evaluation and Research, Summary Review of Application No. 22-184 (Lumigan@ 0.01%) (Jul. 2010).

De Clercq, P. et al., "Cyclopentanones-VXL., Prostaglandin Synthesis Involving Catalytic Hydrogenation of 2,3-Dialkyl-4-Hydroxy-2-Cyclopentenones," Tetrahedron: vol. 32, pp. 2747-2752 (1976).

Deardorff, Dwight et al., "Ophthalmic Preparation," in Remington's Pharmaceutical Sciences 1488 (15th ed. 1975).

Dubiner, Harvey et al., "Efficacy and Safety of Bimatoprost in Patients With Elevated Intraocular Pressure: a 30-Day Comparison With Latanoprost," 45 (4) Surv. Ophthalmol S353-60 (2001).

Gandolfi, Stefano et al., "Three-month Comparison of Bimatoprost and Latanoprost in Patients With Glaucoma and Ocular Hypertension," 18 Adv Ther 110-21 (2001).

Giuffrè, Giuseppe, "The Effects of Prostaglandin F2α in the Human Eye," 222 Graefe's Archive Clin. & Exper. Ophthal. 139 (1985).

Handbook of Pharmaceutical Excipients, Monographs for Water, Sodium Phosphate, Sodium Chloride, and Citric Acid Monohydrate (1994).

Honohan, Thomas et al., "Duration of Activity of the Acid, Methyl Ester and Amide of an Orally Active Platelet Aggregation Inhibitory Prostanoid in the Rat," 19 Prostoglandins 139 (1980).

Katz, Jay et al., "Twelve-Month, Randomized, Controlled Trial of Bimatoprost 0.01%, 0.0125%, and 0.03% in Patients with Glaucoma or Ocular Hypertension," 149(4) Am J. Ophthalmology 661-671 (2010).

Laibovitz, Robert et al., "Comparison of the Ocular Hypotensive Lipid AGN 192024 With Timolol," 119 Arch. Ophthal. 994 (2001).

Lawrence, C.A., "An Evaluation of Chemical Preservatives for Ophthalmic Solutions," 44(8) J. Am. Pharm. Assoc. 457 (1955).

Lawrence, C.A., "Chemical Preservatives for Ophthalmic Solutions," 39 Am. J. Ophthal. 385 (1955).

Martin, F.N. et al., "Preparation of Ophthalmic Solutions With Special Reference to Hydrogen Ion Concentration and Tonicity," 44 Arch. Ophthal. 561 (1950).

Maurice, David, "The Effect of the Low Blink Rate in Rabbits on Topical Drug Penetration," 11(3) J. Ocular Pharmacology and Therapeutics 297-304 (1995).

McPherson, Samuel et al., "Self-Sterilizing Ophthalmic Solutions," 32 Am. J. Ophthalmol. 675 (1949).

Mullen, William et al., "Ophthalmic Preservatives and Vehicles," 17(6) Surv. Ophthal. 469 (1973).

Nilsson, Siv et al., "PGF2α Increases Uveoscleral Outflow," ARVO Abstract, p. 284, Invest. Ophthalmol. Vis. Sci. 28 (1987).

Noecker, Robert et al., "Bimatoprost/Latanoprost Study Group. A Six Month Randomized Clinical Trial Comparing the Intraocular Pressure Lowering Efficacy of Bimatoprost and Latanoprost in Patients With Ocular Hypertension or Glaucoma," 135 Am J. Ophthalmol 55-63 (Jan. 2003).

O'Brien, C.S. et al., "Carbaminoyl-choline Chloride in the Treatment of Glaucoma Simplex," 27 Arch. Ophthal. 253 (1942).

O'Brien, C.S. et al., "Doryl in the Treatment of Glaucoma Simplex," 39 Tran. Am. Ophthal. Soc. 175 (1941).

Parrish, Richard et al., "A Comparison of Latanoprost, Bimatoprost, and Travoprost in Patients With Elevated Intraocular Pressure: A 12-Week, Randomized, Masked Evaluator Multicenter Study," 135 Am J. Ophthalmol 688-703 (2003).

Physicians' Desk Reference, 59th ed., pp. 555-556 (2005).

Physicians' Desk Reference, 56th ed., pp. 212-13, 543, 553-54, 2864-65 (2002).

Roggeband, R. et al., "Eye Irritation in Rabbit and Man After Single Applications of Equal Volumes of Undiluted Model Liquid Detergent Products," 38 Food & Chem. Toxic. 727 (2000).

Sasaki, Hitoshi et al., "Modification of Ocular Permeability of Peptide Drugs by Absorption Promoters," 23(12) Biol. Pharm. Bull. 1524 (2000).

Sasaki, Hitoshi et al., "Ophthalmic Preservatives as Absorption Promoters for Ocular Drug Delivery," 47 J. Pharm. Pharmacol. 703 (1995).

Sasaki, Hitoshi et al., "Ocular Permeability of FITC-Dextran with Absorption Promoter for Ocular Delivery of Peptide Drug," 3 J. Drug Target. 129 (1995).

Skolaut, Milton, "Ophthalmic Medication," 5(4) Bull. Am. Soc. Hosp. Pharm. 172 (1948).

Starr, M.S., "Further Studies on the Effect of Prostaglandin on Intraocular Pressure in the Rabbit," Exp. Eye. Res., 170-177 (1971).

Stern, F.A. et al., "Comparison of the Hypotensive and Other Ocular Effects of Prostaglandins E2 and F2α on Cat and Rhesus Monkey Eyes," 22 Invest. Ophthalmology Visual Sci. 588-98 (1982).

Thygesen, J. et al., "Short-term Effect of Latanoprost and Timolol Eye Drops on Tear Fluid and the Ocular Surface in Patients with Primary Open-Angle Glaucoma and Ocular Hypertension," 78 Acta Ophthalmol. Scand. 37-41 (2000).

Walter, Thomas et al., "24-Hour IOP Control with Once-daily Bimatoprost, Timolol Gel-forming Solution, or Latanoprost: A 1-Month, Randomized, Comparative Clinical Trial," 49 (Supp. 1) Survey of Ophthalmology S26-S35 (2004).

Walter, Modell, "Pharmacologic Action of Some Ophthalmic Drugs," 37 Arch. Ophthal. 160 (1947).

Xu, Ke-Ping et al., "Corneal Organ Culture Model for Assessing Epithelial Responses to Surfactants," 58 Tox. Sci. 306 (2000).

Neal L. Dursrein, "Alteration of Corneal Permeability in Humans and Rabbits" Investigative Ophthalmology & Visual Science / Dec. 1984.

Vincent H.L. Lee, "Review: Topical Ocular Drug Delivery: Recent Developments and Future Challenges", Journal of Ocular Pharmacology, vol. 2, No. 1, 1986, pp. 67-108.

Ola Camber, "Influence of some preservatives on the corneal permeability of pilocarpine and dexamethasone, in vitro", International Journal of Phatmaceurics. 39 (1987) 229-234.

Kazutaka Higaki, "Estimation and enhancement of in vitro corneal transport S-1033, a novel antiglaucoma medication", International Journal of Pharmaceutics 132 (1996) 165 173.

SANDOZ Paragraph4 letter dated Jul. 11, 2011.

Remington's Pharmaceutical Sciences 1501 (15th ed. 1975).

James Leslie Boyd, Quantitative Comparison of Methods of Administering Phvsostigmine, 30 (4) Archives Ophthalmology 521-525 (1943).

H. Barry Collin. Ultrastructural Changes to Corneal Stromal Cells Due to Ophthalmic Preservatives. 64 ACTA Opthalmalogica 72-78 (1986).

Andrew J.W. Huang et al., Paracellular Permeability of Corneal and Conjunctival Epithelia, 30(4) Investigative Opthalmology & Visual Sci., 684-689 (1989).

Komei Okabe et al., Effect of Benzalkoniurn Chloride on Transscleral Drug Delivery, 46 Investigative Ophthalmology & Visual Sci. 703-708 (2005).

Donald J. Lyle, M.D., Early Ocular Manifestations in the Laurence-Moon-Biedl Syndrome, 29 Am J. Ophthalmology 939-946 (1946).

Vincent H. L. Lee & Hans Bundgaard, Improved Ocular Drug Delivery with Prodrugs, in Prodrugs, Topical & Ocular Drug Delivery 221-297 (1992).

Norman F.H. Ho et al., Physical Model Approach to the Design of Drugs with Improved Intestinal Absorption, in Design of Biopharmaceutical Properties through Prodrugs & Analogs, 136-227 (Edward B. Roche ed., 1977).

Laszlo Z. Bito, Prostaglandins, Other Eicosanoids, and Their Derivatives as Potential Antiglaucoma Agents, in Glaucoma: Applied Pharmacology in Medical Treatment 477-505 (1984).

William L. Miller et al.. Biological Activities of 17-Phenyl-18, 19,20-Trinorprostaglandins, 9 Prostaglandins 9 -18 (1975).

Declaration of Larry Wheeler, Ph.D.; Dec. 14, 2010.

Cantor LB, Hoop J, Wudunn D, Yung CW, Valluri S, Cortes A, Acheampong A, Woodward DF, Wheeler LA. Levels of bimatoprost acid in the aqueous humour after bimatoprost treatment of patients with cataract. Br J Ophthalmol. May 2007;91(5):629-32. Epub Nov. 29, 2006.

Davies SS, Ju WK, Neufeld AH, Abran D, Chemtob S, Roberts LJ II. Hydrolysis of bimatoprost (Lumigan) to its free acid by ocular tissue in vitro. J Ocul Pharmacol Ther. Feb. 2003;19(1):45-54.

Camras CB, Toris CB, Sjoquist B, Milleson M, Thorngren JO, Hejkal TW, Patel N, Barnett EM, Smolyak R, Hasan SF, Hellman C, Meza JL, Wax MB, Stjernschantz J. Detection of the free acid of bimatoprost in aqueous humor samples from human eyes treated with bimatoprost before cataract surgery. Ophthalmology. Dec. 2004;111(12):2193-8.

Faulkner R, Sharif NA, Orr S, Sall K, Dubiner H, Whitson JT, Moster M, Craven ER, Curtis M, Pailliotet C, Martens K, Dahlin D. Aqueous humor concentrations of bimatoprost free acid, bimatoprost and travoprost free acid in cataract surgical patients administered multiple topical ocular doses of Lumigan or Travatan. J Ocul Pharmacol Ther. Apr. 2010;26(2):147-56.

Maxey KM, Johnson JL, Labrecque J. The hydrolysis of bimatoprost in corneal tissue generates a potent prostanoid FP receptor agonist. Surv Ophthalmol. Aug. 2002;47 Suppl 1:S34-40.

Bean GW, Camras CB. Commercially available prostaglandin analogs for the reduction of intraocular pressure: similarities and differences. Sury Ophthalmol. Nov. 2008;53 Suppl1:S69-84.

Camras CB, Sharif NA, Wax MB, Stjernschantz J. Bimatoprost, the prodrug of a prostaglandin analogue. Br J Ophthalmol. Jun. 2008;92(6):862-3.

Romano MR, Lograno MD. Evidence for the involvement of cannabinoid CB1 receptors in the bimatoprost-induced contractions on the human isolated ciliary muscle. Invest Ophthalmol Vis Sci. Aug. 2007;48(8):3677-82.

Sharif NA, Kelly CR, Crider JY, Williams GW, Xu SX. Ocular hypotensive FP prostaglandin (PG) analogs: PG receptor subtype binding affinities and selectivities, and agonist potencies at FP and other PG receptors in cultured cells. J Ocul Pharmacol Ther. Dec. 2003;19(6):501-15.

Sharif NA, Klimko, P. Update and commentary on the pro-drug bimatoprost and a putative 'prostamide receptor'. Expert Review of Ophthalmology. Oct. 2009;4(5):477-489.

Alm A, Nilsson SF. Uveoscleral Outflow—A Review. Exp Eye Res. Apr. 2009: 88(4) 760-8. Epub Jan. 3, 2009.

Woodward DF, Krauss AH, Nilsson SFE. Bimatoprost Effects on Aqueous Humor Dynamics in Monkeys. J Ophthalmol. 2010: Article ID 926192, 5 pages.

Sjöquist B, Johansson A, Stjernschantz J. Pharmacokinetics of latanoprost in the cynomolgus monkey. 3rd communication: tissue distribution after topical administration on the eye studied by whole body autoradiography, Glaucoma research laboratories. Arzneim-Forsch/Drug Res 1999:49:240-249.

Woodward DF, Krauss AH, Chen J, et al: The pharmacology of bimatoprost (Lumigan). Surv Ophthalmol 45(Suppl 4): S337-45, 2001.

Woodward DF, Phelps RL, Krauss AH, Weber A, Short B, Chen J, Liang Y, Wheeler LA. Bimatoprost: a novel antiglaucoma agent. Cardiovasc Drug Rev. 2004 Summer;22(2):103-20.

Katz LJ, Ichhpujani P, Hollo G et al. Comparison of Human Ocular Distribution of Bimatoprost and Latanoprost. 2010 (manuscript submitted).

Woodward DF, Krauss AH, Chen J, et al. Pharmacological characterization of a novel anti-glaucoma agent. J. Pharmacol. Exp. Ther. 305:772-85, 2003.

Frenkel RE, Noecker RJ, Craven ER. Evaluation of circadian control of intraocular pressure after a single drop of bimatoprost 0.03% or travoprost 0.004%. Curr Med Res Opin. Apr. 2008;24(4):919-23. Epub Feb. 8, 2008.

Hellberg MR, KE T-L, Haggard K, et al: The hydrolysis of the prostaglandin analog prodrug bimatoprost to 17-phenyltrinor PGF2a by human and rabbit ocular tissue. J Ocular Pharmacol Ther 19:97-103, 2003.

Sjöquist B, Stjernschantz J. Ocular and systemic pharmacokinetics of latanoprost in humans. Surv Ophthalmol. Aug. 2002;47 (Supp 1):S6-12.

Cantor LB. Reply—Bimatoprost, the prodrug of a prostaglandin analogue. Br J Ophthalmol 2008;92:863-864.

Sharif NA, Kelly CR, Crider JY. Human trabecular meshwork cell responses induced by bimatoprost, travoprost, unoprostone, and other FP prostaglandin receptor agonist analogues. Invest Ophthalmol Vis Sci 2003;44:715-21.

Sharif NA, Crider JY, Husain S, et al. Human ciliary muscle cell responses to FP-class prostaglandin analogs: phosphoinositide hydrolysis, intracellular Ca2+ mobilization and MAP kinase activation. J Ocul Pharmacol Ther 2003;19:437-55.

Stamer WD, Piwnica D, Jolas T, Carling RW, Cornell CL, Fliri H, Martos J, Pettit SN, Wang JW, Woodward DF. Cellular basis for bimatoprost effects on human conventional outflow. Invest Ophthalmol Vis Sci. Oct. 2010;51(10):5176-81. Epub Apr. 30, 2010.

Resul B, Stjernschantz J, No K, Liljebris C, Selén G, Astin M, Karlsson M, Bito LZ. Phenyl-substituted prostaglandins: potent and selective antiglaucoma agents. J Med Chem. Jan. 22, 1993;36(2):243-8.

Stjernschantz J. Studies on ocular inflammation and development of a prostaglandin analogue for glaucoma treatment. Exp Eye Res. Apr. 2004;78(4):759-66.

Stjernschantz JW. From PGF2α-isopropyl ester to latanoprost: a review of the development of Xalatan: the Proctor Lecture. Invest Ophthalmol Vis Sci. May 2001;42(6):1134-45.

FDA Label for Approved NDA 22-184 of Lumigan 0.01% and Lumigan 0.03%, Aug. 31, 2010.

Sharif NA, Kaddour-Djebbar I, Abdel-Latif AA. Cat iris sphincter smooth-muscle contraction: comparison of FP-class prostaglandin analog agonist activities. J Ocul Pharmacol Ther. Apr. 2008;24(2):152-63.

Spada CS, Krauss AH, Woodward DF, Chen J, Protzman CE, Nieves AL, Wheeler LA, Scott DF, Sachs G. Bimatoprost and prostaglandin F(2 alpha) selectively stimulate intracellular calcium signaling in different cat iris sphincter cells. Exp Eye Res. Jan. 2005;80(1):135-45.

Woodward, D.F., Krauss, A.H., Wang, J.W., Protzman, C.E., Nieves, A.L., Liang, Y., Donde, Y., Burk, R.M., Landsverk, K., Struble, C. "Identification of an antagonist that selectively blocks the activity of prostamides (prostaglandin ethanolamides) in the feline iris." Br. J. Pharmacol. 150:342-352 (2007).

Liang, Y., Woodward, D.F., Guzman, V.M., Li, C., Scott, D.F., Wang, J.W., et al. (2008). "Identification and pharmacological characterization of the prostaglandin FP receptor and FP receptor variant complexes." Br. J. Pharmacol. 154: 1079-1093.

Van Alphen Gwhm, Wilhelm PB, Elsenfeld PW. The effect of prostaglandins on the isolated internal muscles of the mammalian eye, including man. Documenta Ophthalmologica, 1976, vol. 42, No. 2, pp. 397-415.

Poyer JF, Millar C, Kaufman PL. Prostaglandin F2 alpha effects on isolated rhesus monkey ciliary muscle. Invest Ophthalmol Vis Sci. Nov. 1995;36(12):2461-5.

Yamaji K, Yoshitomi T, Ishikawa H, Usui S. Prostaglandins E1 and E2, but not F2alpha or latanoprost, inhibit monkey ciliary muscle contraction. Curr Eye Res. Aug. 2005;30(8):661-5.

Berglund BA, Boring DL, Howlett AC. Investigation of structural analogs of prostaglandin amides for binding to and activation of CB1 and CB2 cannabinoid receptors in rat brain and human tonsils. Adv Exp Med Biol. 1999;469:527-33.

Cadet P, Mantione KJ, Stefano GB. Molecular identification and functional expression of mu 3, a novel alternatively spliced variant of the human mu opiate receptor gene. J Immunol. May 15, 2003;170(10):5118-23.

Vielhauer GA, Fujino H, Regan JW. Cloning and localization of hFP(S): a six-transmembrane mRNA splice variant of the human FP prostanoid receptor. Arch Biochem Biophys. Jan. 15, 2004;421(2):175-85.

Jordan BA, Devi LA. G-protein-coupled receptor heterodimerization modulates receptor function. Nature. Jun. 17, 1999;399(6737):697-700.

White JH, Wise A, Main MJ, Green A, Fraser NJ, Disney GH, Barnes AA, Emson P, Foord SM, Marshall FH. Heterodimerization is required for the formation of a functional GABA(B) receptor. Nature. Dec. 17, 1998;396(6712):679-82.

Wilson SJ, Roche AM, Kostetskaia E, Smyth EM. Dimerization of the human receptors for prostacyclin and thromboxane facilitates thromboxane receptor-mediated Camp generation. J Biol Chem. Dec. 17, 2004;279(51):53036-47. Epub Oct. 7, 2004.

Crowston et al. Effect of Bimatoprost on Intraocular Pressure in Prostaglandin FP Receptor Knockout Mice. Investigative Ophthalmology and Visual Science, 46:4571-77 (2005).

Response from the Food and Drug Administration to Pfizer's Citizen Petition and a Supplement (Aug. 31, 2010) at 23 (Exhibit 5).

Complaint for Patent Infringment: Civil Action No. 1:10-Cv-681; *Allergan, Inc. and Duke University* V. *Apotex Inc. and Apotex Corp.*; Filed Sep. 8, 2010.

Answer, Defences and Counterclaims of Defendants Apotex Inc. and Apotex Corp,. Civil Action No. 10-Cv-681; *Allergan, Inc. and Duke University* v. *Apotex Inc. and Apotex Corp.*

Asbjorn Tonjum, Permeability of Rabbit Corneal Epithelium to Horseradish Peroxidase After the Influence of Benzalkonium Chloride, Acta Ophthalmologica, Jan. 22, 1975, vol. 53, p. 335-347.

Diane Tang-Liu, Effects of Four Penetration Enhancers on Corneal Permeability of Drugs in Vitro, Journal of Pharmaceutical Sciences, 1994, vol. 83(1), p. 85-90.

George Grass, Mechanisms of Corneal Drug Penetration I: In Vivo and In Vitro Kinetics, Journal of Pharmaceutical Sciences, Jan. 1988, vol. 77(1), p. 3-14.

Keith Green, Influence of Various Agents on Corneal Permeability, American Journal of Ophthalmology, 1971, vol. 72, p. 897-905.

Martina Scholz, Pilocarpine Permeability Across Ocular Tissues and Cell Cultures: Influence of Formulation Parameters, Journal of Ocular Pharmacology and Therapeutics, 2002, vol. 18(5), p. 455-468.

Paul Ashton, Formulation Influence on Conjunctival Penetration of Four Beta Blockers in the Pigmented Rabbit: A Comparison with Corneal Penetration, Pharmaceutical Research, 1991, vol. 8(9), p. 1166-1174.

Pierre-Jean Pisella, Conjunctival Proinflammatory and Proapoptotic Effects of Latanoprost and Preserved and Unpreserved Timolol: An Ex Vivo and In Vitro Study, Investigative Ophthalmology & Visual Science, 2004, vol. 45, p. 1360-1368.

Pieter Van Der Bijl, Effects of Three Penetration Enhancers on Transcorneal Permeation of Cyclosporine, Cornea, 2001, vol. 20(5), p. 505-508.

Samir Podder, Improving the Safety of Topically Applied Timolol in the Pigmented Rabbit Through Manipulation of Formulation Composition, Exp. Eye Res., 1992, vol. 54, p. 747-757.

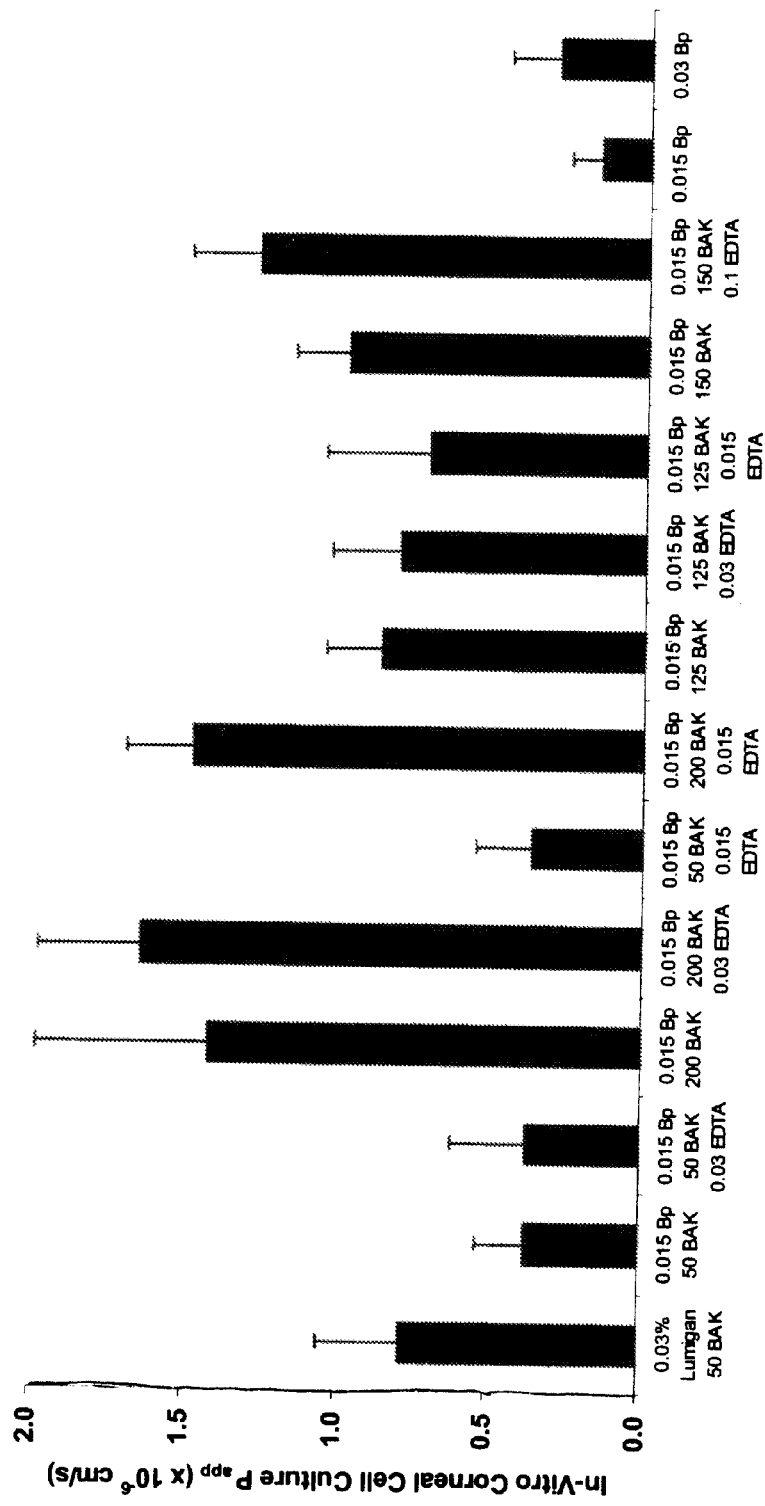

ENHANCED BIMATOPROST OPHTHALMIC SOLUTION

CROSS-REFERENCE TO RELATED APPLICATION

This application is a continuation of U.S. patent application Ser. No. 11/083,261, filed Mar. 16, 2005, which is incorporated herein by reference in its entirety.

FIELD OF THE INVENTION

This invention relates to pharmaceutical compositions comprising bimatoprost.

BACKGROUND OF THE INVENTION

Description of Related Art

Bimatoprost, shown below, is a prostamide marketed commercially for the treatment of glaucoma and ocular hypertension.

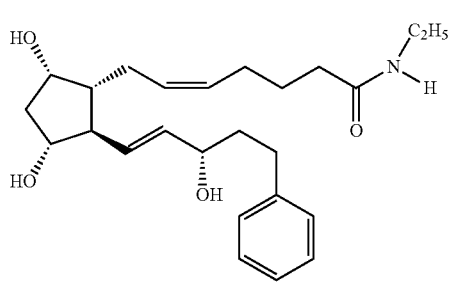

Formula I

Benzalkonium chloride (BAK) is a preservative used in many commercial ophthalmic products to prevent microbial contamination in multi-use products. The commercial eye drops (Bimatoprost, Allergan, Inc., Irvine, Calif.) contain 0.03% bimatoprost and 0.005% BAK. Although no other prostamides are currently marketed for the treatment of glaucoma, several prostaglandin analogs are commercially available which use BAK as a preservative. These include latanoprost (Xalatan), travoprost (Travatan), and unoprostone isopropyl (Rescula), which require significantly more BAK, from 150-200 ppm, to meet antimicrobial effectiveness tests in the United States and Europe.

U.S. Pat. No. 6,596,765 B2 discloses a composition comprising 0.005% or 0.0005% latanoprost and 0.2 mg/mL BAK.

U.S. Pat. No. 6,646,001 B2 discloses compositions comprising 0.03% bimatoprost and 0.01% BAK or "0.01%+5% excess" BAK.

BRIEF DESCRIPTION OF THE DRAWING FIGURES

FIG. 2 is a plot showing the membrane permeability of bimatoprost in several different formulations.

DETAILED DESCRIPTION OF THE INVENTION

Figure 1:
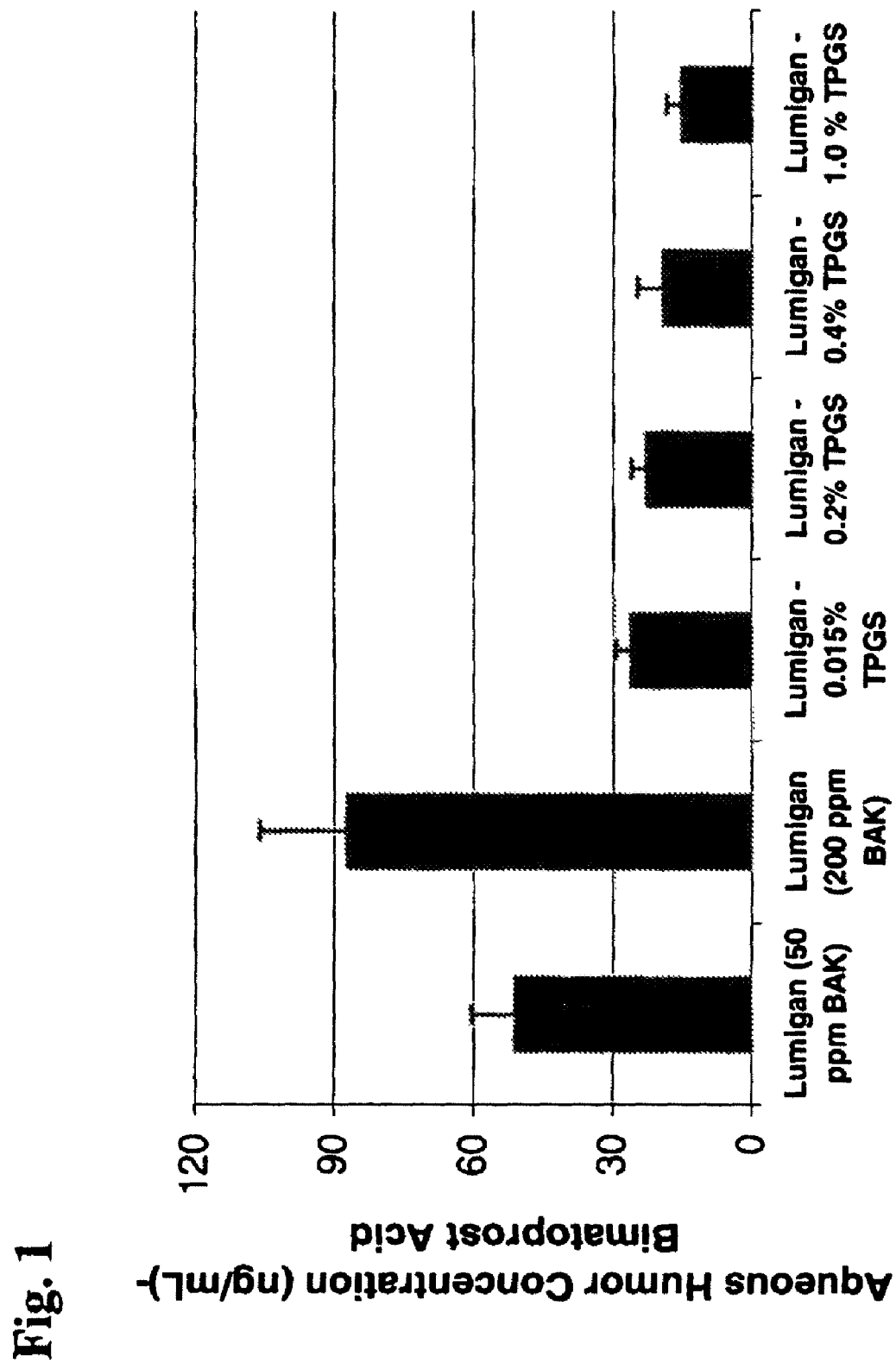
FIG. 1 is a plot showing the aqueous humor concentration of the parent acid of bimatoprost after topical administration of several formulations.

A composition comprising from 0.005% to 0.02% bimatoprost by weight and from 100 ppm to 250 ppm benzalkonium chloride, wherein said composition is an aqueous liquid which is formulated for ophthalmic administration is disclosed herein.

A method which is useful in treating glaucoma or ocular hypertension related thereto is also disclosed herein.

An aqueous liquid which is formulated for ophthalmic administration is formulated such that it can be administered topically to the eye. The comfort should be maximized as much as possible, although sometimes formulation considerations (e.g. drug stability) may necessitate less than optimal comfort.

In certain compositions the concentration of bimatoprost is from 0.01% to 0.02%. In other compositions the concentration of bimatoprost is from 0.015% to 0.02%.

In certain compositions the concentration of BAK is from 150 ppm to 200 ppm. In other compositions the concentration of BAK is from 150 ppm to 200 ppm. In other compositions the concentration of BAK is from 150 ppm to 250 ppm.

In ophthalmic compositions, a chelating agent may be used to enhance preservative effectiveness. Suitable chelating agents are those known in the art, and, while not intending to be limiting, edetate salts (EDTA) are useful chelating agents.

In certain compositions, concentration of EDTA is at least 0.001%. In other compositions, the concentration of EDTA is at least 0.01%. In other compositions the concentration of EDTA is 0.15% or less. In other compositions the concentration of EDTA is 0.1% or less. In other compositions the concentration of EDTA is 0.05% or less.

Certain compositions comprise from 150 to 250 ppm BAK and an effective amount of EDTA.

As is known in the art, buffers are commonly used to adjust the pH to a desirable range for ophthalmic use. Generally, a pH of around 6-8 is desired, and in certain compositions a pH of 7.4 is desired. Many buffers including salts of inorganic acids such as phosphate, borate, and sulfate are known.

Another commonly used excipient in ophthalmic compositions is a viscosity-enhancing, or a thickening agent. Thickening agents are used for a variety of reasons, ranging from improving the form of the formulation for convenient administration to improving the contact with the eye to improve bioavailability. The viscosity-enhancing agent may comprise a polymer containing hydrophilic groups such as monosaccharides, polysaccharides, ethylene oxide groups, hydroxyl groups, carboxylic acids or other charged functional groups. While not intending to limit the scope of the invention, some examples of useful viscosity-enhancing agents are sodium carboxymethylcellulose, hydroxypropylmethylcellulose, povidone, polyvinyl alcohol, and polyethylene glycol.

In ophthalmic solutions, tonicity agents often are used to adjust the composition of the formulation to the desired isotonic range. Tonicity agents are well known in the art and some examples include glycerin, mannitol, sorbitol, sodium chloride, and other electrolytes.

One composition has a pH of 7.4 and consists essentially of 0.015% bimatoprost, 200 ppm benzalkonium chloride, from 0 to 0.03% EDTA, a phosphate buffer, NaCl, and water.

Another composition has a pH of 7.4 and comprises 0.02% bimatoprost, 200 ppm benzalkonium chloride, from 0 to 0.03% EDTA, a phosphate buffer, NaCl, and water.

Another composition has a pH of 7.4 and consists of 0.01% bimatoprost, 200 ppm benzalkonium chloride, from 0 to 0.03% EDTA, a phosphate buffer, NaCl, and water.

The best mode of making and using the present invention are described in the following examples. These examples are given only to provide direction and guidance in how to make and use the invention, and are not intended to limit the scope of the invention in any way.

One embodiment comprises 0.01% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment comprises 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment comprises 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, 0.03%, EDTA, and water, wherein the pH is 7.3.

Another embodiment comprises 0.02% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists essentially of 0.01% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists essentially of 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists essentially of 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, 0.03%, EDTA, and water, wherein the pH is 7.3.

Another embodiment consists essentially of 0.02% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists of 0.01% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists of 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

Another embodiment consists of 0.015% Bimatoprost, 0.02% Benzalkonium Chloride, 0.268% Sodium Phosphate Dibasic, Heptahydrate, 0.014% Citric Acid, Monohydrate, 0.81% Sodium Chloride, 0.03%, EDTA, and water, wherein the pH is 7.3.

Another embodiment consists of 0.02% Bimatoprost, 0.02% Benzalkonium Chloride, 0.268% Sodium Phosphate Dibasic, Heptahydrate, 0.014% Citric Acid, Monohydrate, 0.81% Sodium Chloride, and water, wherein the pH is 7.3.

EXAMPLE 1

Formulations containing 0.268% sodium phosphate dibasic heptahydrate, 0.014% citric acid, 0.83% sodium chloride, with the pH adjusted to 7.3 in qs water, and the amounts of bimatoprost, BAK, and EDTA listed in Table 1 below were prepared by conventional methods well known in the art.

TABLE 1

| Formulation |
| --- |
| 1. 0.03% Bimatoprost (50 ppm BAK) Control |
| 2. 0.03% Bimatoprost - 200 ppm BAK |
| 3. 0.03% Bimatoprost - 0.015% TPGS (no preservative) |
| 4. 0.03% Bimatoprost - 0.2% TPGS (no preservative) |
| 5. 0.03% Bimatoprost - 0.4% TPGS (no preservative) |
| 6. 0.03% Bimatoprost - 1.0% TPGS (no preservative) |

EXAMPLE 2

Studies were carried out to determine the effect of benzalkonium chloride (BAK) and d-alpha tocopheryl polyethylene glycol 1000 succinate (TPGS) on ocular absorption of bimatoprost in vivo. For the in vivo study, eighteen female rabbits were given a single 28 µL eyedrop bilaterally and aqueous humor samples were collected (n=3 animals with 6 eyes per formulation) at 60 min postdose. Two rabbits (4 eyes) remained untreated to serve as pre-dose bioanalytical controls. Bimatoprost and its parent carboxylic acid extracted from aqueous humor and in vitro samples were analyzed by a liquid chromatography tandem mass spectrometry (LC-MS/MS) method with a quantitation range of 0.25-60 ng/mL.

Due to extensive metabolism of bimatoprost in rabbit eyes, its parent acid was used as a surrogate for determining ocular absorption of bimatoprost. Concentration of the acid in rabbit aqueous humor following single dose of 6 different bimatoprost formulations are summarized in FIG. 1 and Table 2 below.

TABLE 2

| Formulation | Aqueous Humor[a] (ng/mL) |
| --- | --- |
| 1. 0.03% Bimatoprost (50 ppm BAK) Control | 51.0 ± 9.4 |
| 2. 0.03% Bimatoprost - 200 ppm BAK | 87.2 ± 19.0* |
| 3. 0.03% Bimatoprost - 0.015% TPGS (no preservative) | 26.1 ± 3.3* |
| 4. 0.03% Bimatoprost - 0.2% TPGS (no preservative) | 22.9 ± 3.2* |
| 5. 0.03% Bimatoprost - 0.4% TPGS (no preservative) | 19.3 ± 5.6* |
| 6. 0.03% Bimatoprost - 1.0% TPGS (no preservative) | 15.4 ± 3.3* |

[a]Mean ± SD. Per formulation, N = 3 rabbits (6 eyes).
*Statistically different (p < 0.05) compared to 0.03% Bimatoprost Test formulations containing 0.015%, 0.2%, 0.4% and 1.0% TPGS resulted in a lower aqueous humor carboxylic acid concentration compared to Bimatoprost by 52%, 59%, 62% and 72%, respectively. In contrast, 0.03% Bimatoprost containing 200 ppm BAK resulted in 57% higher aqueous humor AGN 191522 concentration compared to Bimatoprost (50 ppm BAK).

While not intending to limit the scope of the invention in any way, or be bound by theory, compared to the Bimatoprost control, formulations containing TPGS resulted in decrease bimatoprost permeability. In contrast, formulations with higher BAK resulted in higher permeability.

EXAMPLE 3

Formulations containing 0.268% sodium phosphate dibasic heptahydrate, 0.014% citric acid, 0.83% sodium chloride, with the pH adjusted to 7.3 in qs water, and the amounts of bimatoprost, BAK, and EDTA listed in Table 3 below were prepared by conventional methods well known in the art.

TABLE 3

Formulation

A. 0.03% Bimatoprost (50 ppm BAK) - Control
B. 0.015% Bimatoprost (50 ppm BAK)
C. 0.015% Bimatoprost (50 ppm BAK) 0.03% EDTA
D. 0.015% Bimatoprost (200 ppm BAK)
E. 0.015% Bimatoprost (200 ppm BAK) 0.03% EDTA
F. 0.015% Bimatoprost (50 ppm BAK) 0.015% EDTA
G. 0.015% Bimatoprost (200 ppm BAK) 0.015% EDTA
H. 0.015% Bimatoprost (125 ppm BAK)
I. 0.015% Bimatoprost (125 ppm BAK) 0.03% EDTA
J. 0.015% Bimatoprost (125 ppm BAK) 0.015% EDTA
K. 0.015% Bimatoprost (150 ppm BAK)
L. 0.015% Bimatoprost (150 ppm BAK) 0.1% EDTA
M. 0.015% Bimatoprost
N. 0.03% Bimatoprost

EXAMPLE 4

The effect of benzalkonium chloride (BAK) and ethylenediaminetetraacetic acid (EDTA) on bimatoprost permeability across primary culture of rabbit corneal epithelial cell layers (RCECL). Corneal epithelial cells were harvested from New Zealand White rabbits and cultured on Transwell™ filters until confluency (Day 5). For the transport experiment, cells were first equilibrated in transport buffer for 1 hour at 37° C. Dosing solution containing 0.015% or 0.03% bimatoprost with varying concentrations of BAK and EDTA was then applied to the apical compartment of the Transwell™ (2 cultures; n=3-4 per culture) and the cells were incubated at 37° C. At 30, 60, 90 and 120 minutes postdose, 200 μL samples were taken from the basolateral chamber for apical to basolateral (AB) transport. The samples were analyzed by a liquid chromatography tandem mass spectrometry (LC-MS/MS) method with quantitation range of 1-600 ng/mL.

The results are presented in FIG. 2.

EXAMPLE 5

A drop of formulation J is administered once daily topically to the eye of a person suffering from glaucoma. After a few hours, intraocular pressure drops more and less hyperemia is observed than would be observed for formulation A. Lowered intraocular pressure persists for as long as the treatment continues.

What is claimed is:

1. A method of lowering elevated intraocular pressure in a patient with open-angle glaucoma or ocular hypertension which comprises applying to the eyes of the patient an aqueous solution comprised of:
   about 0.01% w/v bimatoprost;
   about 200 ppm benzalkonium chloride;
   the solution having a pH of about 7.3;
   a phosphate buffer; and,
   water.

2. The method of claim 1 wherein the bimatoprost is present in a concentration of 0.01% w/v and the phosphate buffer is dibasic sodium phosphate.

3. The method of claim 1 further comprising 0.03% EDTA.

4. The method of claims 1 or 2 wherein the patient applies the aqueous solution at least once a day.

5. The method of claim 4 wherein the patient applies the aqueous solution once a day.

6. A method of lowering intraocular pressure in a patient suffering from elevated intraocular pressure which comprises applying to the eyes of the patient an aqueous solution comprising:
   0.01% w/v bimatoprost;
   about 200 ppm benzalkonium chloride;
   the solution having a pH of about 7.3;
   a citric acid buffer; and,
   water.

7. The method of claim 6 wherein the method is applied to patients suffering from glaucoma.

8. The method of claim 6 wherein the citric acid buffer is present in a concentration of about 0.01% w/v.

9. The method of claim 6 wherein the method is applied once a day.

10. The method of claim 7 wherein the glaucoma is open angle glaucoma.

11. The method of claim 6 wherein the solution comprises 200 ppm benzalkonium chloride.

12. A method of treating glaucoma in a patient comprising the following steps:
   applying at least once a day a formulation comprising:
   about 0.01% w/v bimatoprost;
   benzalkonium chloride in the amount of about 200 ppm;
   at least one buffering agent selected from the group consisting of dibasic sodium phosphate heptahydrate, citric acid monohydrate and EDTA;
   and wherein the formulation has a pH of about 7.3.

13. The method of claim 12 wherein the formulation is an aqueous solution.

14. The method of claim 12 wherein the buffering agent is dibasic sodium phosphate heptahydrate.

15. The method of claim 12 wherein the buffering agent is citric acid monohydrate.

16. The method of claim 12 wherein the buffering agent is EDTA.

17. The method of claim 13 further comprising purified water.

18. A method of lowering elevated intraocular pressure in a patient with open-angle glaucoma or ocular hypertension which comprises applying to the eyes of the patient an aqueous solution comprising:
   0.01% w/v bimatoprost;
   0.02% w/v benzalkonium chloride;
   at least two buffering agents selected from the group consisting of dibasic sodium
   phosphate heptahydrate, citric acid monohydrate and EDTA;
   hydrochloric acid and sodium hydroxide to adjust the solution to a pH of about 7.3;
   sodium chloride; and,
   purified water.

19. The method of claim 18 wherein one of the buffering agents is citric acid monohydrate.

20. The method of claim 18 wherein the solution is applied to the patient's eyes at least once a day.

21. The method of claim 18 wherein one of the buffering agents is dibasic sodium phosphate heptahydrate.

* * * * *